(12) United States Patent  
Pazenok et al.

(10) Patent No.: US 9,302,994 B2  
(45) Date of Patent: Apr. 5, 2016

(54) PROCESS FOR THE PREPARATION OF 5-FLUORO-1H-PYRAZOLES

(71) Applicant: BAYER CROPSCIENCE AG, Monheim (DE)

(72) Inventors: Sergii Pazenok, Solingen (DE); Norbert Lui, Odenthal (DE); Vadim Mikhailovich Timoshenko, Kiev (UA); Elena Ivanovna Kaminskaya, Kiev (UA); Yuriy Grigoverievich Shermolovich, Kiev (UA)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/414,254

(22) PCT Filed: Jul. 17, 2013

(86) PCT No.: PCT/EP2013/065094  
§ 371 (c)(1),  
(2) Date: Jan. 12, 2015

(87) PCT Pub. No.: WO2014/012975  
PCT Pub. Date: Jan. 23, 2014

(65) Prior Publication Data  
US 2015/0152062 A1 Jun. 4, 2015

(30) Foreign Application Priority Data

Jul. 19, 2012 (EP) .................................... 12177058

(51) Int. Cl.  
C07D 231/16 (2006.01)

(52) U.S. Cl.  
CPC .................................. C07D 231/16 (2013.01)

(58) Field of Classification Search  
CPC .................................................. C07D 231/16  
See application file for complete search history.

(56) References Cited

U.S. PATENT DOCUMENTS 5,254,774 A 10/1993 Prokop

FOREIGN PATENT DOCUMENTS

SU 1456419 A1 2/1989  
WO 2010051926 A2 5/2010

OTHER PUBLICATIONS

International Search Report from corresponding PCT/EP2013/065094, mailed Jul. 13, 2013.  
Chi et al., "Synthesis of Fluorinated N-arylpyrazoles with Perfluoro-2-methyl-2-pentene and Arylhydrazines", Journal of Fluorine Chemistry, Elsevier, NL, vol. 98, No. 1, Aug. 10, 1999, pp. 29-36, XP004173716.  
I.L Knunyants et al., Izv. Akad. Nauk SSSR, 542.91: 547.773.1, 1990, pp. 2583-2589.  
Haszeldiner et al., Journal of the Chemical Society [Section] D: Chemical Communications, 1970, 21, pp. 1444-1446.

*Primary Examiner* — Samantha Shterengarts  
(74) *Attorney, Agent, or Firm* — McBee Moore Woodward & Vanik IP, LLC

(57) ABSTRACT

A new process for the preparation of 5-fluoro-1H-pyrazoles of the general formula (I)

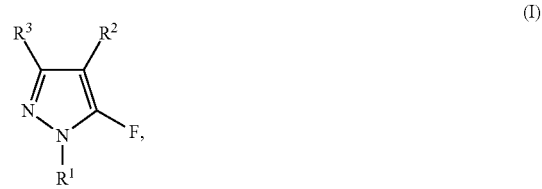

is described, resulting from the reaction of an olefin of the general formula (II)

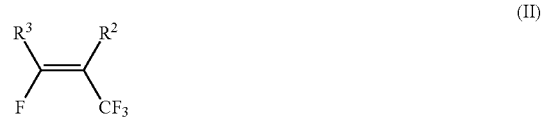

with hydrazines of the formula (III)

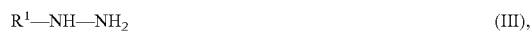

wherein  
$R^1$ is selected from $C_1$-$C_6$ alkyl, $C_5$-$C_{10}$ aryl;  
$R^2$ is a trihalomethyl moiety with at least one fluorine atom; and  
$R^3$ is selected from $C_1$-$C_5$ haloalkyl, $CF_3$, $C_2F_5$, $C_3F_7$, $CF_2CF_2Cl$, $CFClCF_3$,  
in the presence of water and a base.

4 Claims, No Drawings

PROCESS FOR THE PREPARATION OF 5-FLUORO-1H-PYRAZOLES

CROSS REFERENCE TO RELATED APPLICATIONS

This application is a §371 National Stage Application of PCT/EP2013/065094, filed Jul. 17, 2013, which claims priority to EP 12177058.0, filed Jul. 19, 2012.

BACKGROUND

1. Field of the Invention 5-fluoro-1H-pyrazoles, in particular 5-Fluoro-1-methyl-3-pentafluoroethyl-4-trifluoromethyl-1H-pyrazole, are important building blocks for the preparation of crop protection chemicals, as those described in WO 2010051926.

2. Description of Related Art

It is known that 5-fluoro-1-methyl-3-pentafluoroethyl-4-trifluoromethyl-1H-pyrazole can be prepared by the treatment of the dimer of hexafluoropropene with water free N,N-dimethylhydrazine in diethyl ether at −50° C. followed by heating of the intermediate at 120° C., I. L. Knunyants et al. Izv. Akad. Nauk SSSR, (1990) 2583-2589.

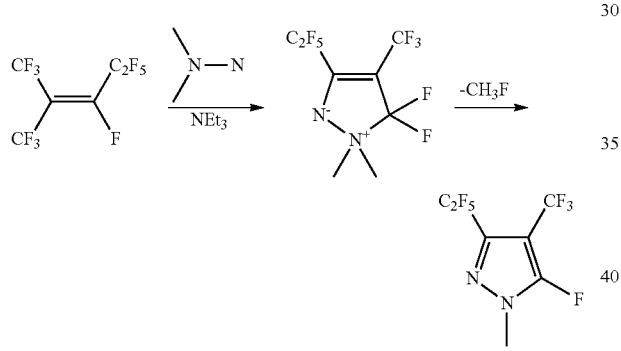

However, this two step transformation requires low temperatures for the first step and results in the formation of $CH_3F$ during the thermal elimination in the second step, making this process expensive, environmentally unfriendly, and particularly difficult for industrialization Starting from perfluoro-2-methyl-2-penten and phenylhydrazine, in the presence of triethylamine at −50° C. 1-Phenylpyrazole was prepared in 90% yield (SU 1456419). Furin et al. J. Fluor. Chem. 98(1999) 29 reported that the areaction of perfluoro-2-methyl-2-penten with phenylhydrazine in $CH_3CN$ gave a mixture of isomeric pyrazoles 3 and 4 in a ratio 4:1.

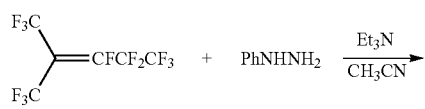

The utilization of the commercially available and cheap monoalkylhydrazines (especially in the form of their water solutions) for the regioselective synthesis of the said pyrazoles is not known to the person of ordinary skill in the art.

SUMMARY

The problem to be solved by this invention was to identify a simple and selective process for preparing 5-fluoro-1H-pyrazoles from available fluoroalkenes and mono-substituted hydrazines, which should in particular be amenable for an industrial scale process.

Surprisingly, 5-fluoro-1H-pyrazoles of the general formula (I)

(I)

can be prepared in high purity and in a short and simple process by reacting an olefins of the general formula (II)

(II)

with a monoalkyl/arylhydrazine of the formula (III)

$$R^1—NH—NH_2 \quad (III),$$

in the presence of water and a base,
wherein
$R^1$ is selected from $C_1$-$C_6$ alkyl, cycloalkyl, $C_5$-$C_{10}$ aryl;
$R^2$ is a trihalomethyl moiety with at least one fluorine atom; and
$R^3$ is selected from $C_1$-$C_5$ haloalkyl as $CF_3$, $CF_2Cl$, $C_2F_5$, $C_3F_7$, $CF_2CF_2Cl$, $CFClCF_3$

DETAILED DESCRIPTION OF A PREFERRED EMBODIMENT

A preferred embodiment of the present invention relates to a process for preparing pyrazoles of formula (Ia),

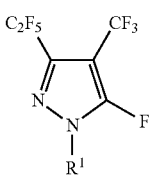

wherein $R^1$ is selected from $C_1$-$C_6$ alkyl, and which comprises the reaction of perfluoro-2-methyl-2-pentene

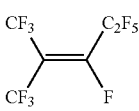

with a monoalkylhydrazine of the general formula (III).

A most preferred embodiment of the present invention relates to a process for preparing pyrazoles of formula (Ib),

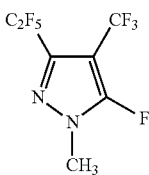

Perfluoro-2-methyl-2-pentene is commercially available (Fa Daikin) and P&M Invest (Russia) or can be prepared via dimerization of hexafluoropropene, see U.S. Pat. No. 5,254,774; R. Haszeldiner et al, Journal of the Chemical Society [Section] D: Chemical Communications (1970), (21), 1444-5.

Monoalkylhydrazines and Monoarylhydrazines are commercially available chemicals.

Preferably $R^1$ is selected from alkyl, very preferably it is methyl.

Preferably $R^2$ is selected from $CF_3$, $CF_2Cl$, very preferably it is $CF_3$.

Preferably $R^3$ is $CF_3$, $C_2F_5$, $C_3F_7$, $CF_2CF_2Cl$, $CFClCF_3$, very preferably it is, $C_2F_5$.

Most preferable are $R^1$=Me, $R^2$=$CF_3$, $R^3$=$C_2F_5$.

Surprisingly, is has been found that the interaction of fluoroalkenes of the formula (II) with water and a base followed by a reaction with hydrazine of the formula (III) proceeds regioselectively with the formation of only one isomeric pyrazole of the formula (I) in a high yield.

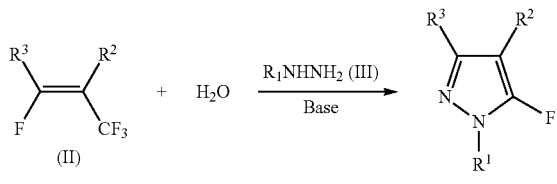

The reaction is performed in the presence of water. According to a further preferred embodiment of the present invention, the amount of water used in the reaction is between 1 and 15 equivalents, preferably 1.5 and 7 equivalents, more preferably 1 and 5 equivalents per one equivalent of the compound of formula (II).

The reaction can be performed in the presence of organic and inorganic bases. Preferred organic bases are: triethylamine, tripropylamine, tributylamin, methydiisopropylamin, N-methylmorpholine, pyridine, alkylpyridines.

Preferred inorganic bases to carry out the reaction are: $NaHCO_3$, $K_2CO_3$, NaOH, $NaHCO_3$, KF The amount of base is selected between 1 and 7 equivalents, preferably between 1.5 and 5 equivalents, more preferably between 1.5 and 3.5 equivalents per one equivalent of the compound of formula (II).

The cyclisation is performed in different solvents selected from alkanes like hexanes, cyclohexane, methylcyclohexane, haloalkanes preferably dichlorometane, dichlorethane, alcohols, preferably methanol, ethanol, or isopropanol, nitriles, preferably acetonitrile, or butyronitrile, amides, preferably dimethylformamide, or dimethylacetamide, ethers like diethylether, methyltert.butylether, dimethoxyethane, diglym, benzene, toluene, dichlorobenzene, chlorobenzene.

Particularly preferred solvents for the cyclisation are dichloromethane, dichloroethane, acetonitrile and butyronitrile, most preferred solvents for this reaction are dichloromethane, acetonitrile and butyronitrile According to a further embodiment of the present invention, the cyclization is performed at a temperature ranging from $-5°$ C. to $50°$ C., more preferably at a temperature ranging from $0°$ C. to $30°$ C., most preferably from $0°$ C. to room temperature.

Generally, the reaction time is not of critical importance and can depend on the reaction volume, preferably it is within the range of 3 and 20 h. more preferably within the range of 1 and 5 h.

The ratio of the compound of formula (III) and the compound of formula (II) can vary within a large range, preferably it is within 0.9 and 1.5 equivalents, more preferably between 1 to 2.5 equivalents, even more preferably between 1 to 1.5, and most preferably 1 equivalent of (III) per one equivalent of the compound of formula (II).

Example 1

N-Methyl-3-Pentafluoroethyl-4-Trifluoromethyl-5-Fluoro-1H-Pyrazole

In a 3-kneck flask equipped with condenser, thermometer, and a dropping funnel 130 ml methylene chloride and perfluoro-2-methyl-2-pentene (19.6 g, 0.065 mol) was placed and then 15 ml water were added. The mixture was cooled to $0°$ C. and $Et_3N$ (16.4 g, 0.16 mol) was added at a temperature ranging from $0°$ C. to $5°$ C. The mixture was stirred at this temperature for 15 min and 40% solution of methylhydrazine in water (7.4 g) was slowly added to this mixture at $0°$ C. The reaction mixture was stirred for 1 h at $5°$ C. and finally for 1.5 h at $20°$ C. The mixture was washed with water (3×50 ml), the organic layer was dried over $Na_2SO_4$ and the solvent was distilled off under atmospheric pressure. The crude product was purified via vacuum distillation. The yield of N-methyl-3-pentafluoroethyl-4-trifluoromethyl-5-fluoro-1H-pyrazole was 13.9 g. (75%), boiling point 62-65° C. at 17 mbar.

Example 2

N-Methyl-3-Pentafluoroethyl-4-Trifluoromethyl-5-Fluoro-1H-Pyrazole

In a 2l 3-kneck flask equipped with condenser, thermometer, and a dropping funnel 1300 ml methylene chloride and perfluoro-2-methyl-2-pentene (197 g, 0.65 mol) was placed, and then 117 ml water were added. The mixture was cooled to −0° C. and $Et_3N$ (164 g, 1.62 mol) was added at a temperature ranging from −5° to 5° C. The mixture was stirred at this temperature for 15 min and a solution of 75 ml N-methylhydrazine in water (40% w.w.) was slowly added to this mixture at 5° C. within 2 h. The reaction mixture was stirred for 15-20 h at 20° C. The mixture was washed with water, the organic layer was dried over $Na_2SO_4$ and the solvent was distilled off under atmospheric pressure. The crude product was purified via vacuum distillation. The yield of N-Methyl-3-pentafluoroethyl-4-trifluoromethyl-5-fluoro-1H-pyrazole was 158 g (85% yield). Boiling point 62-67° C. at 15-20 mbar.

$^{19}F$ NMR δ: 53.7 (3F), 83.9 (3F), 112.1 (2F), 125.1 (1F) ppm.

Example 3

Similarly prepared N-Ethyl-3-pentafluoroethyl-4-trifluoromethyl-5-fluoro-1H-pyrazole from perfluoro-2-methyl-2-pentene and N-Ethylhydrazine Yield 83%, boiling point 70° C. at 18-20 mbar.

The invention claimed is:

1. A process for synthesis of 5-fluoro-1H-pyrazole of formula (I)

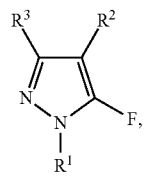

comprising reacting an olefin of formula (II)

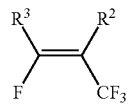

with a hydrazine of formula (III)

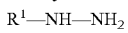

wherein
$R^1$ is selected from $C_1$-$C_6$ alkyl;
$R^2$ is a trihalomethyl moiety with at least one fluorine atom; and
$R^3$ is selected from $C_1$-$C_5$ haloalkyl,
in the presence of water and a base.

2. A process according to claim 1, wherein
$R^1$ is methyl,
$R^2$ is $CF_3$, and
$R^3$ is $C_2F_5$.

3. A process according to claim 1, wherein the base is triethylamine.

4. A process according to claim 1, wherein
$R^2$ is $CF_3$ and
$R^3$ is $C_2F_5$.

* * * * *